(12) United States Patent
Berler et al.

(10) Patent No.: US 11,154,663 B2
(45) Date of Patent: Oct. 26, 2021

(54) PRE-FILLED SAFETY NEEDLE AND SYRINGE SYSTEM

(71) Applicant: Sharps Technology Inc., Melville, NY (US)

(72) Inventors: Barry Berler, Huntingdon Valley, PA (US); Anthony F. Mulone, Jr., Marstons Mills, MA (US); Kevin Corely, Waltham, MA (US); Niv Yaari, Rosh HaAyin (IL); Gil Katz, Avtalyon (IL); Gregory Udovich, Haifa (IL)

(73) Assignee: Sharps Technology Inc., Melville, NY (US)

( * ) Notice: Subject to any disclaimer, the term of this patent is extended or adjusted under 35 U.S.C. 154(b) by 134 days.

(21) Appl. No.: 16/660,784

(22) Filed: Oct. 22, 2019

(65) Prior Publication Data

US 2020/0129707 A1 Apr. 30, 2020

Related U.S. Application Data

(60) Provisional application No. 62/750,780, filed on Oct. 25, 2018.

(51) Int. Cl.
*A61M 5/32* (2006.01)
*A61M 5/315* (2006.01)
(Continued)

(52) U.S. Cl.
CPC .......... *A61M 5/3257* (2013.01); *A61M 5/286* (2013.01); *A61M 5/3134* (2013.01);
(Continued)

(58) Field of Classification Search
CPC ............ A61M 5/31511; A61M 5/3257; A61M 5/3134; A61M 5/286; A61M 5/347;
(Continued)

(56) References Cited

U.S. PATENT DOCUMENTS

| 4,559,043 A | 12/1985 | Whitehouse et al. |
| 5,104,384 A | 4/1992 | Parry |

(Continued)

FOREIGN PATENT DOCUMENTS

| CA | 2236049 | 7/2006 |

*Primary Examiner* — Nathan R Price
*Assistant Examiner* — Justin L Zamory
(74) *Attorney, Agent, or Firm* — LaMorte & Associates P.C.

(57) ABSTRACT

A needle and pre-filled syringe system that provides ultra-low dosage waste and automatic needlestick protection. A syringe assembly is pre-filled with an injection material. A needle head assembly attaches to the syringe assembly. A spacer is disposed between the needle head assembly and the syringe assembly. The spacer has a central opening. The needle head assembly supports a needle with a needle base. When assembled, the needle base passed into the central opening of the spacer. The needle head assembly also contains a safety slide that can selectively cover the needle. During an injection, pressure and/or contact with the plunger head causes the spacer to contact and move the safety slide. The safety slide moves to cover the needle during the injection procedure, therein rendering the needle safe before the injection process is even complete.

18 Claims, 6 Drawing Sheets

(51) Int. Cl.
  *A61M 5/31*  (2006.01)
  *A61M 5/28*  (2006.01)
  *A61M 5/34*  (2006.01)
  *A61M 5/50*  (2006.01)

(52) U.S. Cl.
  CPC ...... *A61M 5/31511* (2013.01); *A61M 5/3286* (2013.01); *A61M 5/3293* (2013.01); *A61M 5/347* (2013.01); *A61M 5/5086* (2013.01); *A61M 2005/3131* (2013.01); *A61M 2205/583* (2013.01)

(58) Field of Classification Search
  CPC .............. A61M 5/5086; A61M 5/3286; A61M 5/3293; A61M 5/31535; A61M 2005/31516; A61M 2005/3131; A61M 2005/311; A61M 2005/31598; A61M 2005/3132; A61M 2005/2462; A61M 2005/2474; A61M 2205/583
  See application file for complete search history.

(56) References Cited

U.S. PATENT DOCUMENTS

| | | |
|---|---|---|
| 5,306,258 A | 4/1994 | de la Fuente |
| 5,314,503 A | 5/1994 | Bobrove et al. |
| 5,370,628 A | 12/1994 | Allison et al. |
| 5,385,555 A | 1/1995 | Hausser |
| 5,460,611 A | 10/1995 | Alexander |
| 5,733,264 A | 3/1998 | Flowers |
| 5,891,092 A | 4/1999 | Castellano |
| 5,902,270 A | 5/1999 | Jentzen |
| 6,616,636 B2 | 9/2003 | Lee |
| 6,626,863 B1 * | 9/2003 | Berler .................. A61M 5/326 604/110 |
| 2007/0016140 A1 | 1/2007 | Berler |
| 2007/0016145 A1 | 1/2007 | Berler |
| 2008/0009808 A1 | 1/2008 | Berler |
| 2008/0319346 A1 | 12/2008 | Crawford et al. |
| 2016/0279333 A1 | 9/2016 | Russo et al. |
| 2016/0279344 A1 | 9/2016 | Shluzas et al. |
| 2017/0319791 A1 | 11/2017 | Giambattista et al. |

* cited by examiner

PRE-FILLED SAFETY NEEDLE AND SYRINGE SYSTEM

RELATED APPLICATIONS

This application claims the benefit of U.S. provisional patent application No. 62/750,780, filed Oct. 25, 2018.

BACKGROUND OF THE INVENTION

1. Field of the Invention

In general, the present invention relates to pre-filled syringes that are used to make injections through a needle or cannula. More particularly, the present invention relates to needle and syringe systems where the needle automatically becomes shielded after use.

2. Prior Art Description

Millions of injections are performed in the United States of America each year. The injections are typically performed using a hypodermic needle and a syringe. The length of the hypodermic needle and the gauge of the needle depend upon the application and whether the injection is intramuscular, subcutaneous, intravenous, or intradermal. The compounds being injected also vary widely. Many pharmaceutical compounds, such as certain gene therapy compounds, can cost tens of thousands of dollars per injection. As such, a fraction of a milliliter of the pharmaceutical can be worth hundreds of dollars.

Some pharmaceutical compounds are manufactured as pre-filled syringes. That is an exact dose of a pharmaceutical compound is loaded into a syringe by the manufacturer. The syringe is sealed and is sent to healthcare providers. The healthcare providers attach needle heads to the pre-filled syringes and administer the injection to patients. When a traditional needle head is used to perform an injection, there is inevitably some volume of injection material that remains within the needle head after the injection is complete. As such, the full dosage contained within the pre-filled syringe is not transferred to the patient. The pharmaceutical material remaining in the needle head is thrown away after the injection. This wasted pharmaceutical material adds up to billions of dollars in wasted pharmaceuticals, when all injections are considered.

In the prior art, thought is rarely given to the volume of residual material that inherently remains within a needle head. Some needle and syringe assemblies have been designed where a syringe plunger and a needle head make flush contact. Such prior art designs are exemplified by U.S. Pat. No. 6,616,636 to Lee and U.S. Pat. No. 5,902,270 to Jentzen. However, in a real healthcare environment, such as a hospital, pre-filled syringes are used with many different needle heads, depending upon the injection being made. Some needle head and syringe combinations are efficient in the discharge of pharmaceutical compounds and some are not.

The problem becomes more complicated when a needle head used with a pre-filled syringe contains safety features. Some needle heads are designed to both perform an injection and to provide some mechanism for minimizing the likelihood of a needlestick injury. Needlestick injuries are commonplace among healthcare workers. Needlestick injuries are defined by the United States National Institute of Occupational Safety and Health as injuries caused by needles such as hypodermic needles, blood collection needles, intravenous (IV) stylets, and needles used to connect parts of IV delivery systems. Needlestick injuries can transfer blood-borne pathogens such as Hepatitis B virus, Hepatitis C virus, and Human Immunodeficiency Virus (HIV). For healthcare workers, needlestick injuries are responsible for a significant portion of these diseases in the healthcare workforce.

It has been estimated by the Center for Disease Control, that in the United States of America, more than three million healthcare workers are exposed to blood and body fluids via needle mishaps each year. Most healthcare workers are trained in procedures for using and disposing of used needles. Used needles should not be recapped in order to prevent the potential for needlestick injuries. However, many studies have revealed that recapping is still prevalent among healthcare workers.

In an attempt to reduce the number of needlestick injuries, various safety needles have been developed that act to cover a needle the instant the needle is retracted from the skin. This is typically accomplished by advancing a tubular sheath along the shaft of the needle until the sheath covers the tip of the needle. Such prior art is exemplified by U.S. Pat. No. 6,626,863 to Berler, U.S. Patent Application Publication No. 2007/0016140 to Berler, U.S. Patent Application Publication No. 2007/0016145 to Berler, and U.S. Patent Application Publication No. 2008/0009808 to Berler. However, integrating a safety mechanism within a needle head typically takes additional room within the needle head. More room in the needle head means that there is more dead space in the needle head where residual pharmaceutical compounds can collect. As a consequence, there are often opposing concerns that must be balanced in a design. The safety features of a design are balanced with the wasted pharmaceutical retained due to safety features.

A need therefore exists for an improved hypodermic needle and pre-filled syringe assembly where the needle is automatically shielded after an injection and wherein the assembly does not retain any significant volume of the material being injected.

This need is met by the present invention as described and claimed below.

SUMMARY OF THE INVENTION

The present invention is a needle and pre-filled syringe system that provides both ultra-low dosage waste and automatic needlestick protection. A syringe assembly is provided that contains a syringe barrel and a plunger. The syringe barrel is pre-filled with an injection material. The plunger has a plunger head that moves in the barrel and can be used to move the injection material toward an open end of the syringe barrel.

A needle head assembly attaches to the syringe assembly prior to use. A spacer is disposed between the needle head assembly and the syringe assembly. The spacer has a central opening that extends through said spacer.

The needle head assembly supports a needle with a needle base. The needle head assembly attaches to the syringe barrel over the open end of the syringe barrel. When assembled, the needle base passes into the central opening of the spacer. The needle head assembly also contains a safety slide that can selectively cover the needle. During an injection, pressure and/or contact with the plunger head causes the spacer to contact and move the safety slide. As such, the safety slide moves to cover the needle during the injection procedure, therein rendering the needle safe before the injection process is even complete.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

The present invention needle and syringe system can be configured in many ways and can be adapted for use in many applications. However, only a few exemplary embodiments are selected for the purposes of description and illustration. The illustrated embodiments, however, are merely exemplary and should not be considered a limitation when interpreting the scope of the appended claims.

Figure 1:
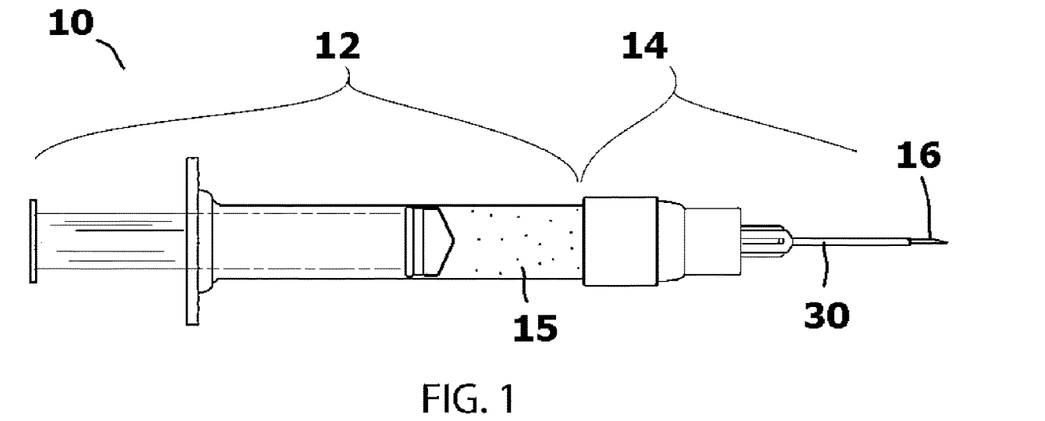
FIG. 1 is a cross-sectional view of an exemplary embodiment of safety needle and syringe system that contains a syringe assembly attached to a needle head assembly.
Figure 2:
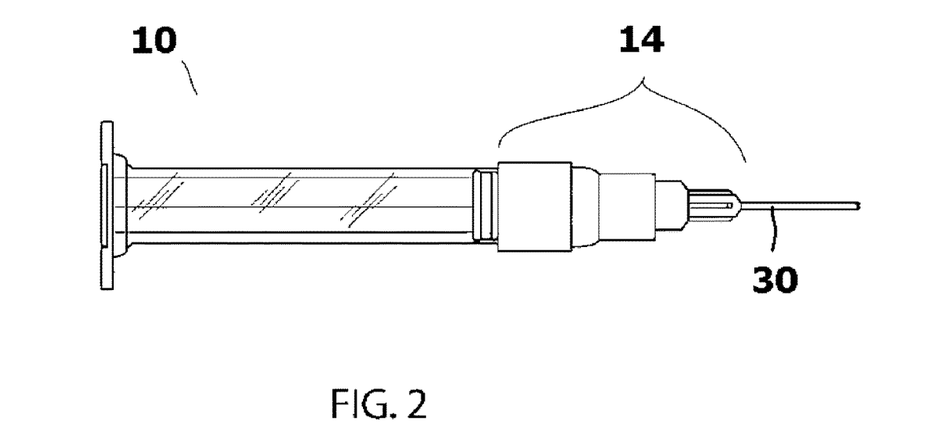
FIG. 2 shows an exploded view of the exemplary embodiment of FIG. 1.
Figure 3:
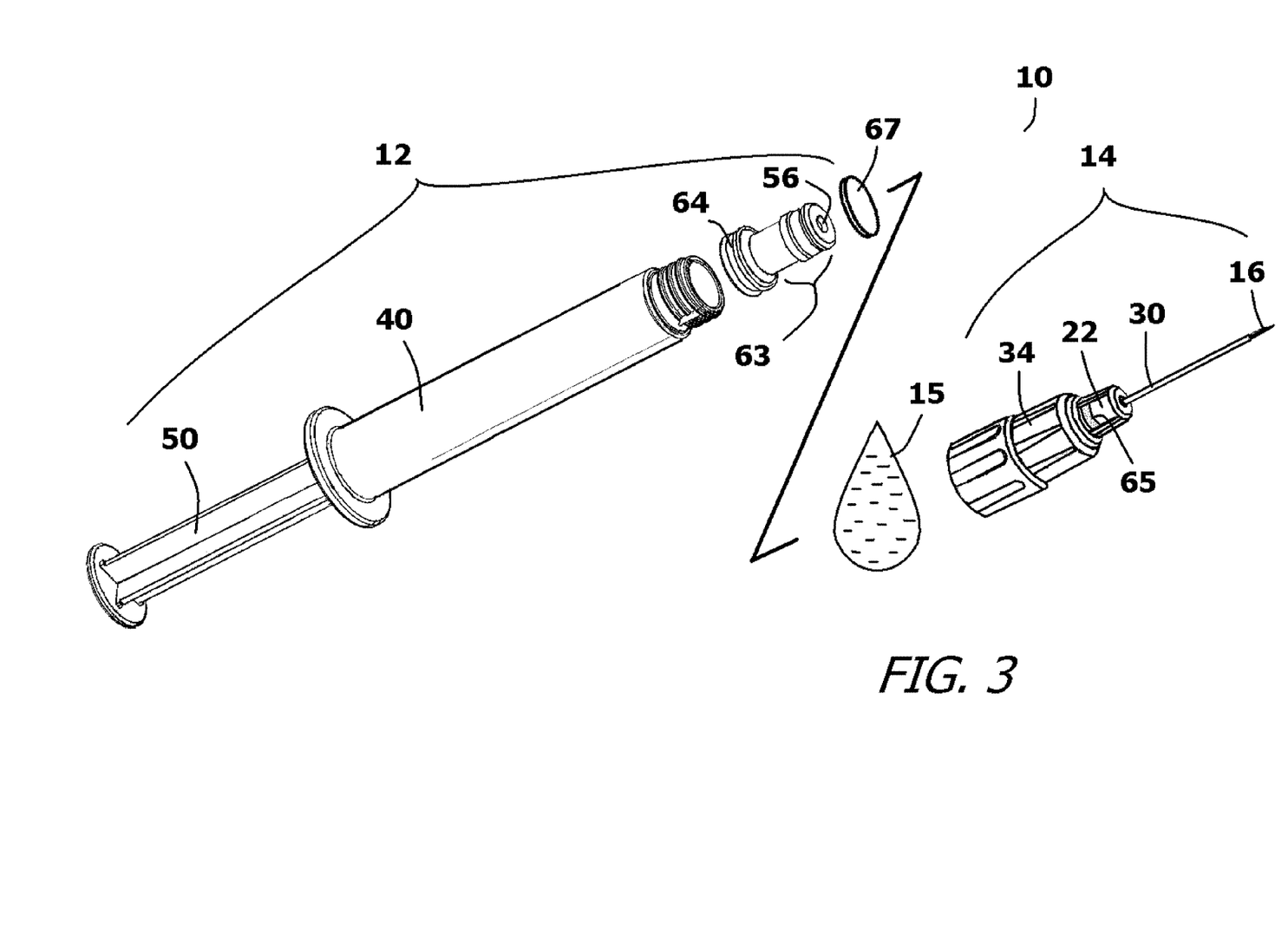
FIG. 3 shows a perspective view of the safety slide component of the needle head assembly.

Referring to FIG. 1, FIG. 2, and FIG. 3, an overview of the present invention needle and syringe system 10 is shown. In the shown embodiment, the needle and syringe system 10 includes two primary assemblies that are selectively joined by a healthcare professional just prior to use. The primary assemblies include a pre-filled syringe assembly 12 and a needle head assembly 14.

The pre-filled syringe assembly 12 contains a volume of injection material 15 that is sealed within the pre-filled syringe assembly 12. When the needle head assembly 14 is attached to the pre-filled syringe assembly 12, the needle head assembly 14 pierces the pre-filled syringe assembly 12 and provides a flow path between the injection material 15 and a hypodermic needle 16. As will be explained in greater detail, the needle 16 is surrounded by a sheathing tube 30. During the injection process, the sheathing tube 30 is advanced over the needle 16, therein rendering the needle 16 safe even before the needle 16 is withdrawn from a patient. The needle 16 is therefore exposed (FIG. 1) prior to beginning an injection procedure and is covered (FIG. 2) by the end of the injection procedure.

Figure 4:
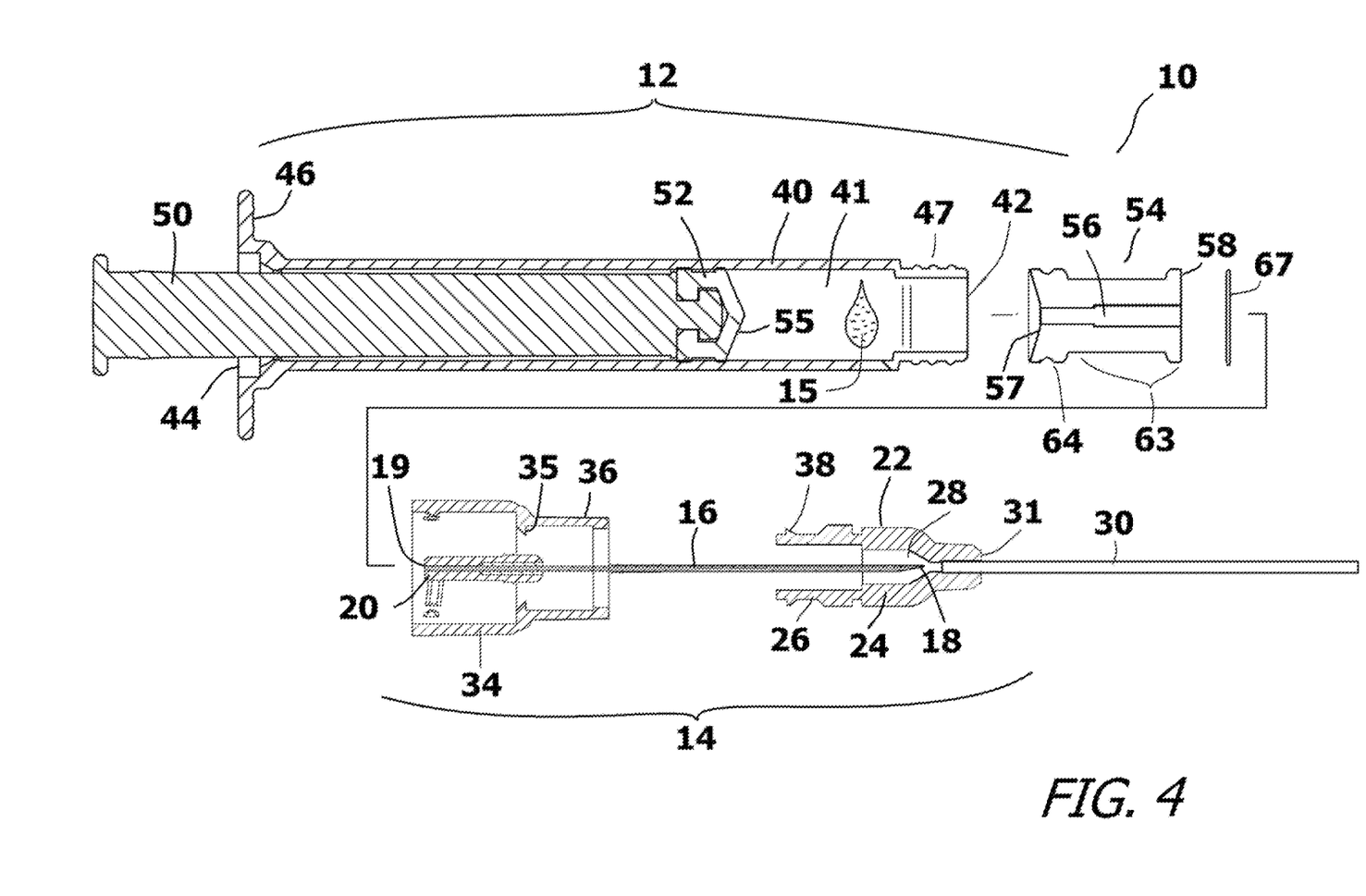
FIG. 4 is an enlarged cross-sectional view of the neck of the syringe assembly and the needle head assembly prior to the activation of the safety slide in the needle head assembly.
Figure 5:
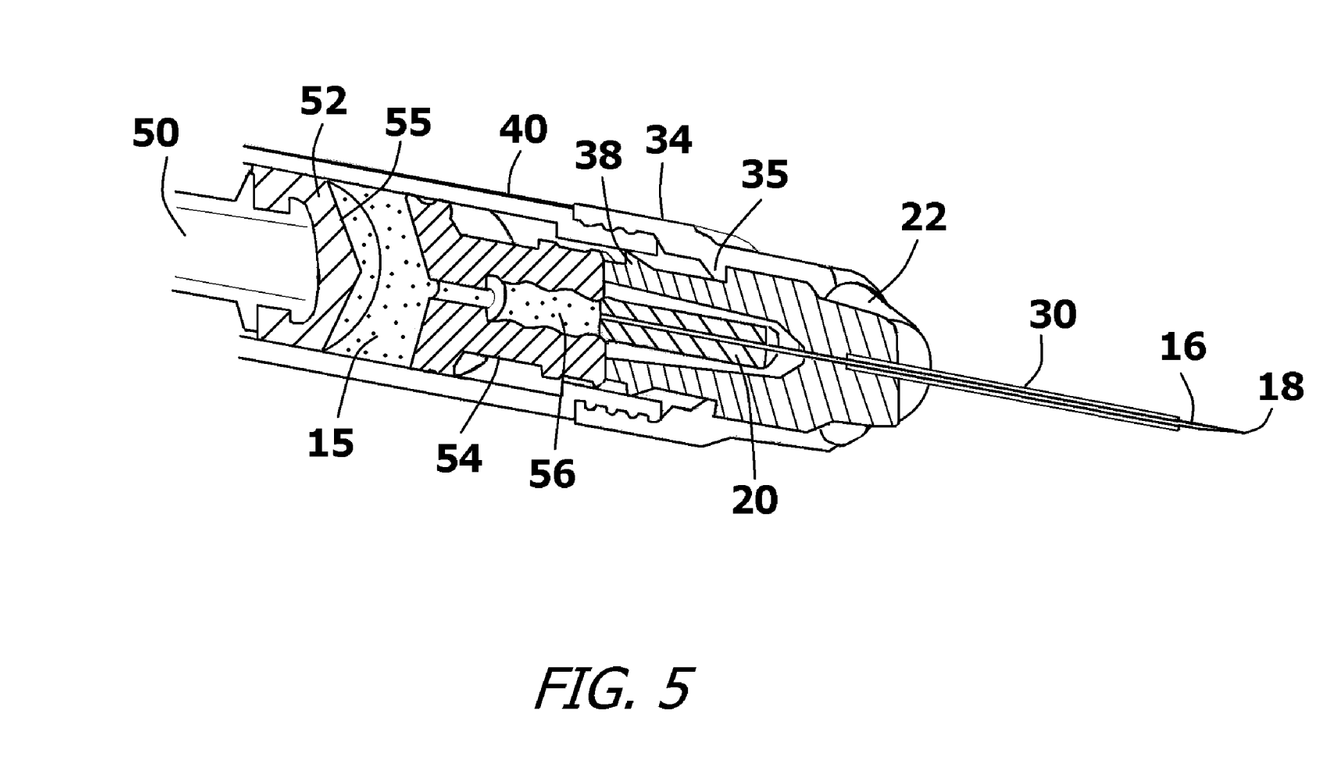
FIG. 5 is an enlarged cross-sectional view of the neck of the syringe assembly and the needle head assembly during the activation of the safety slide in the needle head assembly.

Referring to FIG. 4 and FIG. 5 in conjunction with FIG. 3, it will be understood that the needle head assembly 14 retains the needle 16. The needle 16 has a sharpened first end 18 and an opposite second end 19. Both ends 18, 19 protrude from the needle head assembly 14 in opposite directions. The gauge of the needle 16 and the length of the needle 16 are selected by the healthcare professional for the medical procedure being performed. Within the needle head assembly 14, part of the needle 16 is set into an elongated base 20. The elongated base 20 is tubular and does not obstruct flow through the needle 16. As such, the needle 16 and the elongated base 20 move together as a single unit. The second end 19 of the needle 16 may terminate at the same point as the elongated base 20, as is shown. However, to reduce cost, the needle 16 can end within the elongated base 20 and the elongated base 20 can continue to extend to a salient point in the same direction as the needle 16.

The needle head assembly 14 includes a collar 34 and a safety slide 22. The elongated base 20 of the needle 16 is affixed to the collar 34. As such, during an injection, there is no relative movement between the collar 34, the needle 16, and the elongated base 20. The collar 34 mechanically attaches to the pre-filled syringe assembly 12 with a bayonet connection, a threaded connection, or a similar mechanical connection. As such, the collar 34 is used to interconnect the needle head assembly 14 to the pre-filled syringe assembly 12. The collar 34 has an internal ridge 35, the purpose of which is later described.

A safety slide 22 is positioned inside the collar 34, wherein the safety slide 22 surrounds a section of the needle 16 and the elongated base 20. The safety slide 22 moves relative the needle 16 and the collar 34, wherein the needle 16 and the collar 34 guide the movement of the safety slide 22.

The safety slide 22 has a tubular body 24. Legs 26 extend from a first end 27 of the tubular body 24. Locking protrusions 38 radially extend from the legs 26, for a purpose that is later explained. The tubular body 24 defines a central cavity 28 that is sized to receive the elongated base 20 of the needle 16. A sheathing tube 30 extends from a second end 31 of the safety slide 22 opposite the legs 26. The extending sheathing tube 30 is cantilevered and defines a pathway that communicates with the central cavity 28. The elongated base 20 extends into the central cavity 28 of the safety slide 22 and the needle 16 extends through the sheathing tube 30 of the safety slide 22. As will be explained, the safety slide 22 is able to move relative the needle 16 and the elongated base 20.

The pre-filled syringe assembly 12 has a barrel 40. The barrel 40 defines a tubular chamber 41 that extends between an open first end 42 and an open second end 44. The barrel 40 can be glass or plastic. In the shown embodiment, the barrel 40 as a threaded neck 47. As such, the inner diameter of the barrel 40 is reduced at the transition to the threaded neck 47. The threaded neck 47 is threaded or otherwise configured to be engaged by the collar 34 of the needle head assembly 14. Likewise, the exterior of the barrel 40 at the opposite second end 44 has finger flanges 46, to facilitate the proper gripping of the pre-filled syringe assembly 12.

A plunger 50 is set within the barrel 40. The plunger 50 has a plunger head 52 that seals against the tubular chamber 41 within the barrel 40 as the plunger 50 reciprocally moves within the barrel 40. The plunger head 52 is wider than the threaded neck 47 of the barrel 40 and cannot pass into the threaded neck 47. The plunger head 52 has a face surface 55 that faces the open first end 42 of the barrel 40.

A tubular spacer 54 is positioned within the tubular chamber 41 of the barrel 40. The tubular spacer 54 has a central opening 56 that extends between a first end 57 and a second end 58. The tubular spacer 54 has a narrow section 63 and an enlarged base 64. The enlarged base 64 has the same diameter as the plunger head 52 and seals against the tubular chamber 41 within the barrel 40 in the same manner. As such, fluid can only pass the tubular spacer 54 within the barrel 40 by flowing through the central opening 56 that extends through the tubular spacer 54. The first end 57 of the tubular spacer 54 is oriented toward the face surface 55 of the plunger head 52. The first end 57 of the tubular spacer 54 is configured to abut against the plunger head 52 with no intervening gap spaces. At the opposite second end 58, the central opening 56 in the tubular spacer 54 is sized to receive the elongated base 20 at the bottom of the needle 16.

The tubular spacer 54 is positioned within the tubular chamber 41 of the barrel 40. Initially, the second end 58 of the tubular spacer 54 is flush with the open first end 42 of the barrel 40. The enlarged base 64 of the tubular spacer 54 creates a seal within the barrel 40. A volume of injection material 15 is added into the barrel 40, wherein the injection material 15 is positioned between the plunger head 52 and the tubular spacer 54. When the plunger head 52 is advanced within the barrel 40, the only exit for the injection material 15 is through the central opening 56 of the tubular spacer 54. A seal cover 67 is provided that seals the central opening 56 of the tubular spacer 54 and the first open end 42 of the barrel 40. As such, prior to use, it will be understood that both the injection material 62 and the tubular spacer 54 are sealed within the barrel 40.

Figure 6:
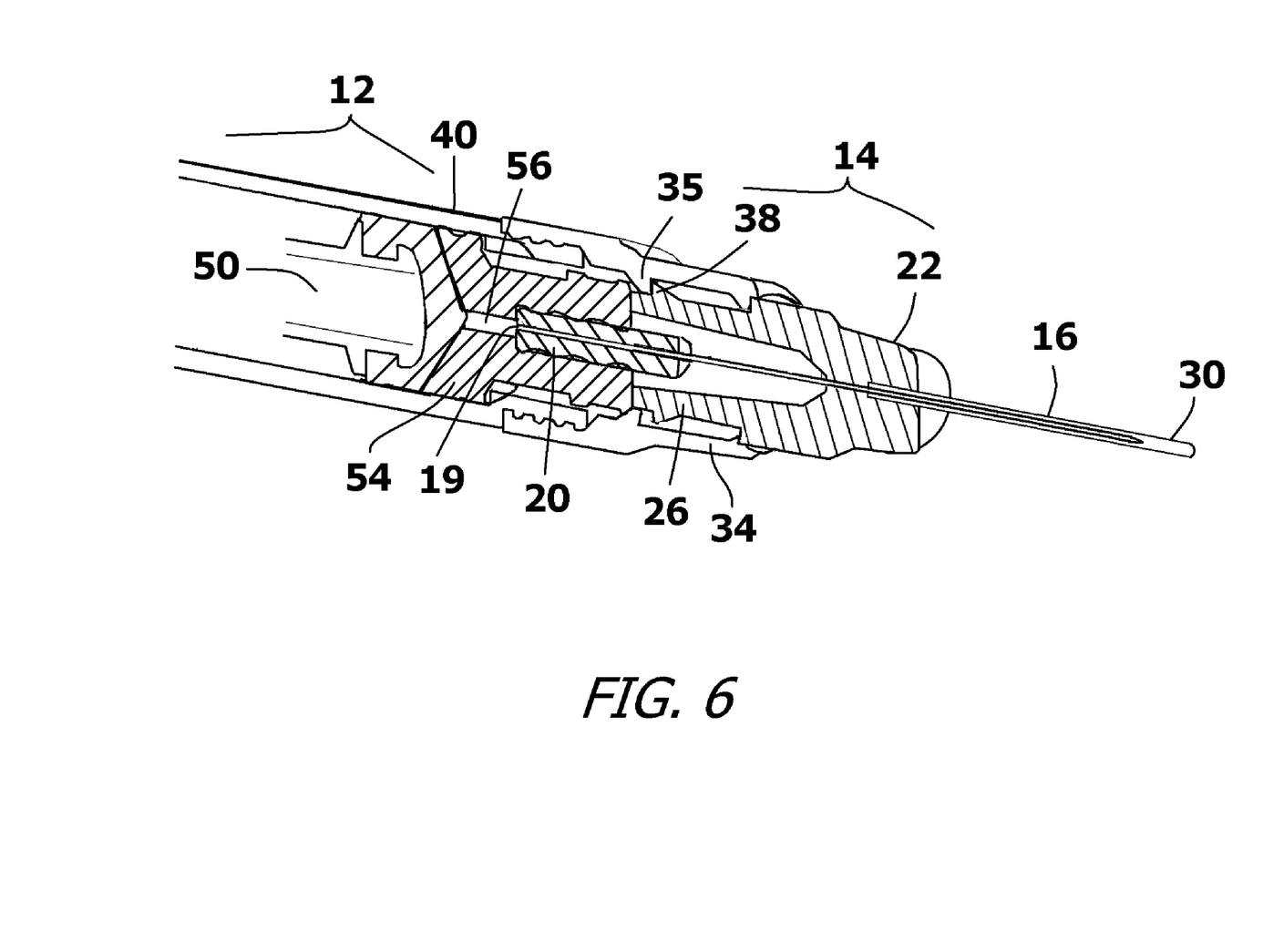
FIG. 6 is an enlarged cross-sectional view of the neck of the syringe assembly and the needle head assembly after the activation of the safety slide in the needle head assembly.

Referring to FIG. 6 in conjunction with FIG. 4 and FIG. 5, it will be understood that when the needle head assembly 14 is attached to the pre-filled syringe assembly 12, the second end 19 of the needle 16 and/or the elongated base 20 of the needle 16 pierces the seal cover 67 on the pre-filled syringe assembly 12. This occurs as the collar 34 of the needle head assembly 14 attaches to the threaded neck 47 of the barrel 40. As the seal cover 67 is pierced, the elongated base 20 of the needle 16 passes into the central opening 56 of the tubular spacer 54. The elongated base 20 passes into the tubular spacer 54 with an interference fit, therein creating a fluid impervious seal between the elongated base 20 and the tubular spacer 54. As a result, the only exit for the injection material 15 is out through the central opening 56 of the tubular spacer 54 and through the needle 16.

It will be understood that in order to utilize the needle and syringe system 10, a needle head assembly 14 and a syringe assembly 12 are selected that are appropriate for the medical injection to be performed. The needle head assembly 14 is manually attached to the pre-filled syringe assembly 12. A precise volume of injection material 15 is contained within the pre-filled syringe assembly 12.

Before use, the sharpened first end 18 of the needle 16 is exposed. The first end 18 of the needle 16 is used to make an injection through a patient's skin. Due to the fineness of the sheathing tube 30, the sheathing tube 30 also typically passes into the skin through the opening made by the needle 16. The injection material 62 is injected by advancing the plunger head 52 toward the needle head assembly 14. As is indicated by FIG. 5 and FIG. 6 in sequence, the needle 16 and the elongated base 20 remain stationary before, during and after an injection. The elongated base 20 partially extends into the central opening 56 of the tubular spacer 54. In this manner, the injection material 15 that flows through the needle 16 can freely flow through the tubular spacer 54.

As the plunger 50 advances in the barrel 40, the injection material 15 is displaced out of the barrel 40 through the needle 16. As the plunger head 52 initially contacts the tubular spacer 54, there are no gap spaces between the plunger head 52 and the tubular spacer 54. The only areas that contain the injection compound 62 are inside the needle 16 and in the central opening 56 of the tubular spacer 54 that is not occupied by the elongated base 20 of the needle 16. However, at this point, the plunger 50 is not yet fully depressed within the barrel 40.

Referring to FIG. 6, it can be seen that as the plunger 50 is advanced, the pressure of the injection material begins to push the tubular spacer 54 into the needle head assembly 14. Toward the end of the injection process, the plunger head 52 contacts and directly pushes the tubular spacer 54. At this point, there is very little open space within the tubular spacer 54. The only place where the injection material 15 can remain is within the needle 16 itself. This area is very small. The result is that very little of the injection material 15 is wasted and nearly all of the volume of injection material 15 contained within the pre-filled syringe assembly 12 is discharged during the injection procedure.

As the tubular spacer 54 is advanced out of the barrel 40 by the plunger head 52, the tubular spacer 54 presses against the legs 26 of the safety slide 22. As a consequence, the safety slide 22 is pushed and moves forward within the surrounding collar 34. As the safety slide 22 moves forward, the sheathing tube 30 is advanced over the needle 16, wherein the sheathing tube 30 eventually extends beyond the sharpened first end 18 of the needle 16. The movement of the safety slide 22 occurs during the injection procedure. The passage of the sheathing tube 30 over the tip of the needle 16 typically occurs before the injection is complete. As such, when the needle 16 is retracted out of the skin, the needle 16 is already covered by the sheathing tube 30. This renders the needle 16 safe.

As the safety slide 22 advances within the stationary collar 34, the locking protrusions 38 on the legs 26 of the safety slide 22 pass over and engage an internal ridge 35 on the interior of the collar 34. This prevents the needle head assembly 14 from being reset and reused. Additionally, as the safety slide 22 advances within the collar 34, a visual indicator 65 (FIG. 3) on the exterior of the safety slide 22 becomes visible. The visual indicator 65 becomes visible as the safety slide 22 locks in engagement with the collar 34. The visual indicator 65 enables a healthcare worker to see that the needle and syringe system 10 has been used and that the system 10 is locked into a safe configuration and is ready for disposal.

In view of the above, it will be understood that prior to use, the safety slide 22 is retracted and the needle 16 extends beyond the sheathing tube 30 where it can be used. During use, the safety slide 22 advances the sheathing tube 30 along the needle 16 to cover the needle 16. After use, the safety slide 22 is fully extended and the sheathing tube 30 covers all of the needle 16, therein rendering the needle 16 safe.

Figure 7:
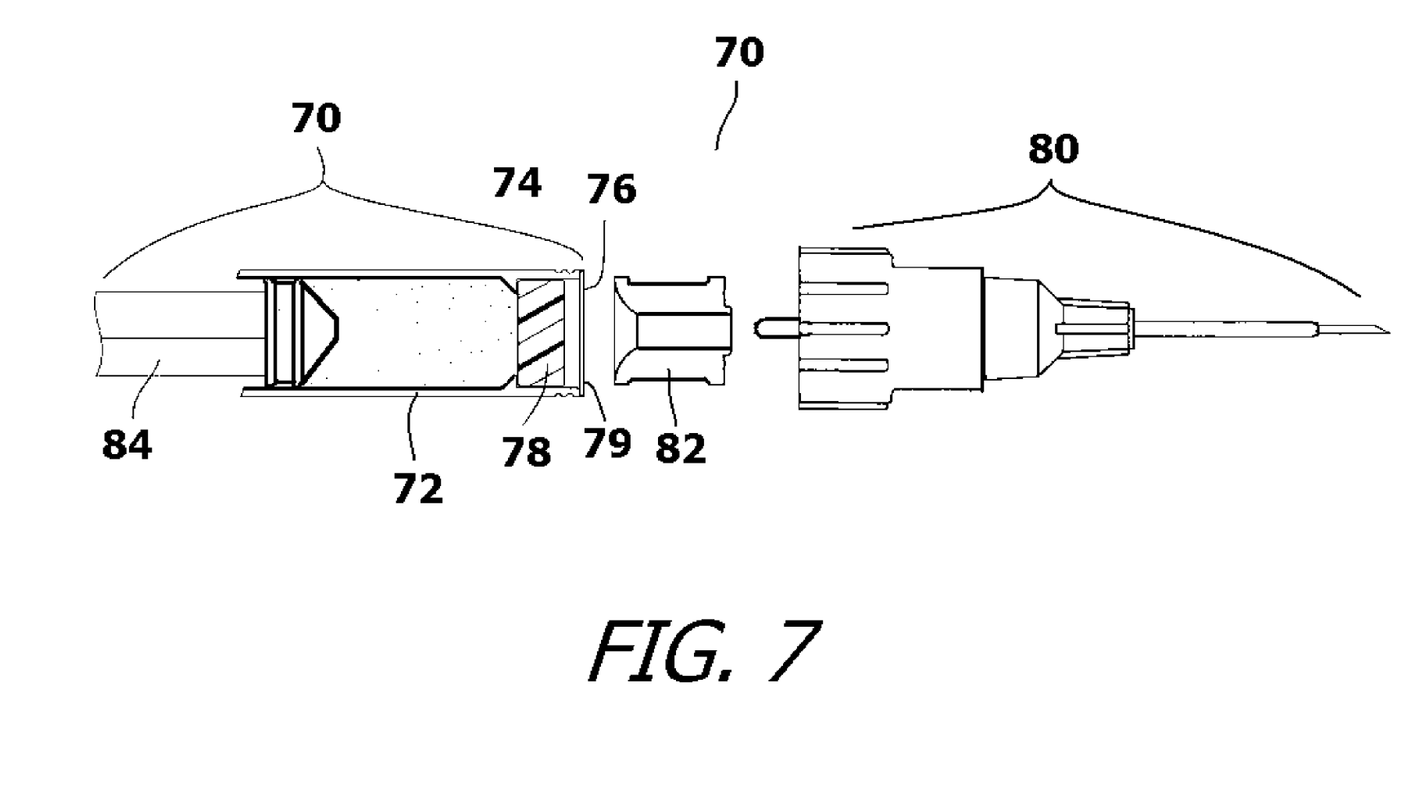
FIG. 7 is a cross-sectional view of an alternate embodiment of a needle and pre-filled syringe assembly.

In the embodiment of FIG. 1 though FIG. 6, the needle and pre-filled syringe system 10 is applied to a syringe barrel 40 with a narrowed threaded neck 47. This is typical for a glass syringe barrel. However, with plastic syringe barrels, the barrels often have a constant diameter between ends. Referring to FIG. 7, a pre-filled syringe assembly 70 is shown that has a constant diameter barrel 72. A ring protrusion 74 is formed in the barrel 72 a short distance from its open end 76. An elastomeric seal 78 is placed in the barrel 72, wherein the elastomeric seal 78 rests upon the ring protrusion 74. The elastomeric seal 78 is protected by a peal-away cover 79.

A needle head assembly 80 is provided that is the same as has been previously described. However, in this embodiment, a tubular spacer 82 is positioned within the needle head assembly 80 rather than in the pre-filled syringe assembly 70. When the needle head assembly 80 is attached to the pre-filled syringe assembly 70, the needle head assembly 80 pierces the elastomeric seal 78 in the pre-filled syringe assembly 70. Once a plunger 84 is moved, the elastomeric seal 78 moves against the tubular spacer 82 and the two components act as a single element. The tubular spacer 82 then activates the safety features embodied in the needle head assembly 80 in the same manner as was previously described in regard to the first embodiment.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A needle and syringe system, comprising:
   a syringe barrel pre-filled with an injection material, wherein said syringe barrel has a first open end;
   a plunger with a plunger head that can be reciprocally moved within said syringe barrel, wherein said plunger head has a face surface that faces said injection material within said syringe barrel;
   a spacer disposed in said syringe barrel, said spacer having a central opening that extends through said spacer and a contact surface that faces said injection material within said syringe barrel;
   a seal that closes said first open end of said syringe barrel, wherein said injection material and said spacer are interposed between said plunger head and said seal within said syringe barrel;
   a needle head assembly that supports a needle, wherein said needle head assembly selectively attaches to said syringe barrel over said first open end, and wherein said needle head assembly pierces said seal and interconnects with said spacer so that said central opening of said spacer is aligned with said needle.

2. The system according to claim 1, wherein said needle head assembly includes a needle base that supports said needle and a collar that selectively connects to said syringe barrel, wherein said needle base is affixed to said collar.

3. The system according to claim 2, wherein said needle base extends into said central opening of said spacer as said collar connects to said syringe barrel.

4. The system according to claim 3, wherein said needle extends between a sharpened first end and an opposite second end, wherein said second end of said needle pierces said seal as said needle head assembly attaches to said syringe barrel.

5. The system according to claim 2, further including a safety slide with a sheathing tube that surrounds part of said needle, and wherein said safety slide can move relative said needle and said collar between a first position, where said sheathing tube covers only part of said needle, and a second position where said sheathing tube covers all of said needle.

6. The system according to claim 5, wherein when said plunger is advanced in said syringe barrel, said plunger head contacts and moves said spacer, said spacer advances over said needle base, and said safety slide moves from said first position to said second position.

7. The system according to claim 6, wherein said needle base moves through said central opening in said spacer to said contact surface of said spacer as said safety slide moves from said first position to said second position.

8. The system according to claim 1, wherein said contact surface of said spacer and said face surface of said plunger head conform so that no spaces exist between said contact surface and said face surface upon contact between said contact surface and said face surface.

9. The system according to claim 5, further including a lock that automatically locks said safety slide in said second position as said safety slide enters said second position.

10. The system according to claim 9, further including a visual indicator on said safety slide that becomes visible when said safety slide enters said second position.

11. A needle and syringe system, comprising:
    a pre-filled syringe assembly that contains a barrel, a plunger and a seal, wherein said plunger has a plunger head and wherein an injection material is held in said barrel between said plunger head and said seal;
    a needle head that selectively attaches to said pre-filled syringe assembly, wherein said needle head supports a needle with a sharpened end and a needle base;
    a tubular spacer disposed in said needle head, wherein said spacer has a central opening extending therethrough, wherein said needle base extends through said central opening.

12. The system according to claim 11, further including a safety slide having a sheathing tube that surrounds part of said needle, and wherein said safety slide can move relative said needle between a first position, where said sheathing tube does not extend beyond said sharpened end of said needle, and a second position where said sheathing tube extends beyond said sharpened end of said needle.

13. The system according to claim 12, wherein when said plunger is advanced in said barrel, said plunger head moves said spacer and said spacer moves said safety slide from said first position to said second position.

14. The system according to claim 11, wherein said needle head pierces said seal as said needle head is attached to said pre-filled syringe barrel.

15. The system according to claim 11, wherein said spacer and said plunger head conform so that no spaces exist between said spacer and said plunger head upon contact between said spacer and said plunger head.

16. The system according to claim 13, wherein said safety slide locks into said second position as said safety slide enters said second position.

17. The system according to claim 16, further including a visual indicator on said safety slide that becomes visible when said safety slide enters said second position.

18. The system according to claim 11, wherein said needle head includes a collar that selectively engages said barrel.

\* \* \* \* \*

UNITED STATES PATENT AND TRADEMARK OFFICE
CERTIFICATE OF CORRECTION

| | | |
|---|---|---|
| PATENT NO. | : 11,154,663 B2 | Page 1 of 1 |
| APPLICATION NO. | : 16/660784 | |
| DATED | : October 26, 2021 | |
| INVENTOR(S) | : Barry Berler et al. | |

It is certified that error appears in the above-identified patent and that said Letters Patent is hereby corrected as shown below:

On the Title Page

At item (71), please amend Applicant to Sharps Technology, Inc.

At item (73), please amend Assignee to Sharps Technology, Inc.

Signed and Sealed this
Nineteenth Day of July, 2022

Katherine Kelly Vidal
*Director of the United States Patent and Trademark Office*